(12) United States Patent
Ideker et al.

(10) Patent No.: US 10,675,477 B2
(45) Date of Patent: Jun. 9, 2020

(54) IMPLANTABLE CARDIOVERTER DEFIBRILLATORS USING HIGH POWER AMPLIFIERS WITH IMPEDANCE TRACKING LOWPASS FILTERS

(71) Applicant: RUSE TECHNOLOGIES, LLC, Brookhaven, GA (US)

(72) Inventors: Raymond E. Ideker, Birmingham, AL (US); Richard Ruse, Brookhaven, GA (US); Scott Bohanan, Statesboro, GA (US)

(73) Assignee: RUSE TECHNOLOGIES, LLC, Brookhaven, GA (US)

(*) Notice: Subject to any disclaimer, the term of this patent is extended or adjusted under 35 U.S.C. 154(b) by 0 days.

(21) Appl. No.: 16/664,285

(22) Filed: Oct. 25, 2019

(65) Prior Publication Data

US 2020/0129776 A1    Apr. 30, 2020

Related U.S. Application Data

(60) Provisional application No. 62/751,142, filed on Oct. 26, 2018.

(51) Int. Cl.
| | |
|---|---|
| *A61N 1/39* | (2006.01) |
| *H03F 3/21* | (2006.01) |
| *H03F 3/217* | (2006.01) |
| *H03H 11/04* | (2006.01) |

(52) U.S. Cl.
CPC ......... *A61N 1/3906* (2013.01); *A61N 1/3956* (2013.01); *A61N 1/39622* (2017.08); *H03F 3/211* (2013.01); *H03F 3/217* (2013.01); *H03F 2200/171* (2013.01); *H03F 2200/321* (2013.01); *H03F 2200/351* (2013.01); *H03F 2203/21157* (2013.01); *H03H 11/04* (2013.01)

(58) Field of Classification Search
CPC .............. A61N 1/3906; A61N 1/39622; A61N 1/3956; H03F 3/211; H03F 3/217; H03F 2203/21157; H03F 2200/171; H03H 11/04
See application file for complete search history.

(56) References Cited

U.S. PATENT DOCUMENTS

| | | | |
|---|---|---|---|
| 4,870,341 A | 9/1989 | Pihl et al. | |
| 5,206,602 A | 4/1993 | Baumgartner et al. | |
| 5,772,692 A | 6/1998 | Armstrong | |
| 6,078,214 A * | 6/2000 | Zhang ................... | H03F 3/2171 330/10 |
| 6,430,449 B1 | 8/2002 | Hsu et al. | |
| 6,438,418 B1 | 8/2002 | Swerdlow et al. | |

(Continued)

*Primary Examiner* — Nathan J Jenness
(74) *Attorney, Agent, or Firm* — William Dippert; Laurence Greenberg; Werner Stemer (57) ABSTRACT

An apparatus has advanced amplifier Classes and low pass filter technologies for using software generated ascending or level waveforms that are effective when applying cardiac defibrillation and cardioversion waveforms which significantly reduce damage to the heart muscle. The apparatus comprises a waveform energy control system for delivering software generated waveforms comprising differentially driven Class D and Class B amplifier sections, wherein the Class D amplifier section produces Phase 1 ascending waveforms and has a programmable lowpass filter (LPF) and wherein the Class B amplifier section delivers hard-switched Phase 2 waveforms.

15 Claims, 7 Drawing Sheets

(56) References Cited

U.S. PATENT DOCUMENTS

| | | |
|---|---|---|
| 6,766,195 B1 | 7/2004 | Bornzin et al. |
| 7,200,434 B2 | 4/2007 | Havel et al. |
| 7,389,140 B1 | 6/2008 | Kroll |
| 7,450,995 B2 | 11/2008 | Moulder et al. |
| 7,555,341 B2 | 6/2009 | Moffitt et al. |
| 7,647,115 B2 | 1/2010 | Levin et al. |
| 7,657,310 B2 | 2/2010 | Buras |
| 7,706,889 B2 | 4/2010 | Gerber et al. |
| 7,920,918 B2 | 4/2011 | Ideker et al. |
| 7,983,748 B2 | 7/2011 | Ruse |
| 7,986,992 B2 | 7/2011 | Ideker et al. |
| 8,175,702 B2 | 5/2012 | Efimov et al. |
| 8,509,889 B2 | 8/2013 | Efimov et al. |
| 8,560,066 B2 | 10/2013 | Efimov et al. |
| 8,639,325 B2 | 1/2014 | Efimov et al. |
| 8,874,208 B2 | 10/2014 | Efimov et al. |
| 9,067,079 B2 | 6/2015 | Efimov et al. |
| 9,526,907 B2 | 12/2016 | Efimov et al. |
| 9,561,383 B2 | 2/2017 | Ideker et al. |
| 9,636,504 B2 | 5/2017 | Gilman et al. |
| 9,757,577 B2 | 9/2017 | Ideker et al. |
| 2003/0045909 A1 | 3/2003 | Gross et al. |
| 2003/0125773 A1 | 7/2003 | Havel et al. |
| 2004/0002736 A1 | 1/2004 | Waltman |
| 2005/0065553 A1 | 3/2005 | Ben Ezra et al. |
| 2005/0107834 A1 | 5/2005 | Freeman et al. |
| 2005/0131475 A1 | 6/2005 | Smits |
| 2006/0074450 A1 | 4/2006 | Boveja et al. |
| 2006/0116736 A1 | 6/2006 | DiLorenzo |
| 2008/0103440 A1 | 5/2008 | Ferren et al. |
| 2010/0217344 A1 | 8/2010 | Carranza et al. |
| 2012/0179218 A1 | 7/2012 | Moulder |
| 2013/0296974 A1 | 11/2013 | Wanasek |
| 2014/0051963 A1* | 2/2014 | Kaib ............... A61B 5/04085 600/388 |
| 2014/0094869 A1 | 4/2014 | Walker et al. |
| 2018/0085594 A1 | 3/2018 | Tandri et al. |

\* cited by examiner

IMPLANTABLE CARDIOVERTER DEFIBRILLATORS USING HIGH POWER AMPLIFIERS WITH IMPEDANCE TRACKING LOWPASS FILTERS

CROSS-REFERENCE TO RELATED APPLICATION

This patent application is based upon and claims the priority of U.S. Provisional Patent Application Ser. No. 62/751,142, filed Oct. 26, 2018, incorporated herein in its entirety by reference.

FIELD OF THE INVENTION

This application relates to implantable and external cardioverter defibrillation devices. More particularly, this application relates to implantable and external cardioverter defibrillation devices comprising Class DB amplifiers that incorporate advanced lowpass filters that eliminate the requirement for large high voltage, high current inductors and capacitors.

BACKGROUND OF THE INVENTION

High voltage cardioverters and defibrillators today typically use an H-Bridge circuit configuration that discharges a charged capacitor for a Phase 1 descending biphasic truncated exponential (BTE) waveform through a diagonal pair of power transistors, MOSFETs, IGBTs, or any other switching devices, through the heart. A Phase 2 waveform is then switched on through a second diagonal transistor pair that delivers voltage and current through the heart, but in a reverse polarity as compared to the Phase 1 waveform. Both of the Phase 1 and Phase 2 waveforms are basically natural capacitive discharge waveforms based upon the "Tilt" equation:

$$V_C = V_O e^{-t/RC} \tag{I}$$

where $V_C$ is the voltage across a capacitor after a certain time period has elapsed; $V_O$ is the initial voltage across the capacitor before the discharging begins when it is connected in series with a resistor in a closed circuit; t is the period of time in seconds which has elapsed since the discharge process began; R is the resistance of the resistor to which the capacitor is connected in the circuit; and C is the capacitance of the capacitor. This voltage decay equation is the solution to a differential equation (based on energy balance) for constant resistance and capacitance (R and C), and the peak voltage and tilt decay are a function of the load impedance as the voltage is delivered through a load or heart muscle in the case of a high voltage cardioversion/defibrillation device or system. Pulse widths in existing ICDs are controlled by microcontroller commands which also contribute to the tilt angle of the waveform.

Class D amplifiers are very efficient and desirable to use. However, when Class D amplifier topologies or circuits are used, it is difficult to miniaturize the pulse width modulation (PWM) switching circuits as well as large and very large high current inductors and capacitors that are characteristic of Class D amplifiers. Therefore, a new approach is required to miniaturize these Class D topologies or circuits for use in implantable cardioverter defibrillator devices (ICDs), subcutaneous cardioverter defibrillator devices (SICDs), or other external or implantable devices without using the large or very large inductors and capacitors as low pass filters.

OBJECTS OF THE INVENTION

It is an object of the invention to provide a novel cardiovascular apparatus comprising a Class D amplifier that efficiently amplifies Phase 1 waveforms and a Class B amplifier that hard switches Phase 2 waveforms which require a fast slew rate (DV/DT) change in voltage over change in time.

It is also an object of the invention that the Class D amplifier comprises a new lowpass filter (LPF) technology.

It is a further object of the invention that the apparatus uses software generated waveforms.

It is a yet further object of the invention that use of the apparatus described herein and ascending waveforms significantly reduce damage to a patient's heart muscle.

It is a yet further object of the invention that the LPF design allows the apparatus to fit into conventional subcutaneously implantable ICD/SICD designs.

It is a yet further object of the invention that the LPF design allows the apparatus to operate within an external defibrillation device.

It is a yet further object of the invention that the LPF design allows the apparatus to be used in any power circuit, motor drive, audio power amplifier, or any high power electronics device that requires a high power LPF to filter out any PWM pulses in place of using large inductors and capacitors.

These and other advantages of the invention will become more apparent in the discussion below.

SUMMARY OF THE INVENTION

The improvements described herein relate to Class DB amplifiers useful for implantable cardioverter defibrillators (ICDs), subcutaneous implantable cardioverter defibrillators (SICDs), external defibrillation devices such as hospital grade and automated external defibrillators (AEDs), as well as EMT/EMS and sports grade cardioversion and defibrillation devices. See FIGS. 1 and 2.

In an aspect of the invention, a novel combination of Class D pulse width modulated (PWM) and Class B amplifier linear circuit architectures (Class DB) is employed and proposed for cardioversion and defibrillation. Two or more differentially driven amplifiers are used for the purpose of cardioversion/defibrillation whereby a Phase 1 waveform is typically a positive ascending voltage waveform with respect to the ground or return pathway for the circuit and a Phase 2 waveform is typically a negative, descending voltage waveform with respect to the ground return.

In the amplifier circuit topologies' normal operation, a Phase 1 waveform signal would be delivered through a Class D amplifier as an ascending, descending, or level arbitrary waveform that is employed as specified by software generated waveforms, which are very accurate and efficient in their delivery and tolerance as compared to a simple capacitor discharge tilt BTE waveform. A Phase 2 waveform signal would also be delivered by software generated waveforms delivered through the second stage of a Class B amplifier circuit.

In accordance with the invention, a combination amplifier (Class DB) comprises Class D circuit architecture whereby a Phase 1 waveform is delivered through a first half of the Class D amplifier circuit and driven differentially through to a second half of the Class D amplifier circuit, to construct and deliver the Phase 1 waveform. Advantageously, Phase 2 waveforms in this new high voltage circuit are delivered through a hard-switched Class B circuit that is an integral part of the amplifier circuits, or can be outside the confines of the amplifier circuits since they are operated in a linear on/off hard switched mode. The Phase 2 waveform can be a software programmed geometry or shape, but also may be a natural capacitor discharge through a hard-switching circuit that discharges the same capacitor that is used by the amplifier to deliver waveforms of the desired pulse shape, width, and tilt angle. This would naturally occur from a capacitive discharge using the same mathematical formulas wherein the remaining stored energy in the capacitor defined as $½ CV^2$ energy (stored in joules) is left in the capacitor after the amplifier portion has delivered a positive ascending Phase 1 waveform such as an ascending ramp waveform.

The advantage to the circuit architecture described herein is having a hybrid approach to cardioversion and/or defibrillation where the Class D designs employ a new LPF for a Phase 1 waveform which does not use high current inductors and capacitors that are too large for proper miniaturization. Instead, smaller Class B Phase 2 waveform semiconductor devices are used due to the very fast slew rates of the Phase 2 waveforms or vertical pulses. Typically, a Phase 2 waveform circuit needs to be a very fast transition from switching Phase 1 waveform depolarization circuits off and turning on the Phase 2 waveform circuits for hyperpolarization pulses which are very short in pulse width and duration, and utilize a natural decay or tilt angle for the capacitor discharge for the Phase 2 waveforms or pulses. These Phase 2 waveforms or pulses are in the approximately 1 ms to 4 ms time periods with no appreciable slope to the rising and falling edges of the Phase 2 waveform. With the use of fast slew rate semiconductor devices as compared to the existing Phase 1 power amplifier devices employed now for waveform delivery, the traditional size of the standard H-Bridge power device footprints as well as the associated drive circuitry can be dramatically reduced. This allows for a higher degree of miniaturization and very high efficiencies may be realized within the device. The size of implantable cardioverter defibrillators is always a concern, and with the use of this new hybrid Class DB circuit topology, power dissipation for Phase 1 and Phase 2 waveforms can be reduced.

The new LPF design described herein incorporates a solid state filter design whereby no large inductors or capacitors are employed.

Due to use of a combination of Class D and Class B amplifiers within one circuit topology along with a microprocessor controlled digital software managed system, the amplifier according to the invention is very efficient in terms of energy transfer functions for cardioversion defibrillation waveform delivery. The design also provides a low ripple modulation post LPF that approaches a noise floor of a linear amplifier. The microcontroller-based LPF provides a rolling average and tunable filter on the fly throughout any delivered waveform selected within a cardioversion device by dynamically tracking the chest and heart impedance.

Issues such as pulseless electrical activity/electromechanical disassociation (PEA/EMD) may benefit from using arbitrary waveform delivery at any voltage amplitude to help a post shock event. The amplifier architecture described herein can deliver any type of waveform shape, amplitude, or pulse width duration to stimulate the heart muscle during that critical time period where the heart is trying to recover from a high voltage shock that perhaps has stunned or damaged the cardiac muscle. The ability to use software generated waveforms delivered through the Class DB amplifier may provide a stimulus that could be very useful to those skilled in the art to keep the heart, and ventricles in particular, stimulated and pumping blood until such time as the heart is capable of delivering the normal SA/AV node pacing stimulation and/or allow an implanted pacing device to continue normal pacing activity post shock if there is a PEA/EMD episode.

Another aspect of the invention comprises an electrical mode whereby the intraventricular septum and bundle branches may be stimulated. For example, during the absolute refractory period the ventricles are stimulated to contract even further than the heart's own stimulus provides during the late systolic contraction period, thus assisting patients with congestive or chronic heart failure (CHF) by increasing the ejection fraction (EF), hopefully above the threshold of 35% as measured by echocardiography. With use of the Class DB amplifier technology described herein, high efficiency energy deliveries using arbitrary ascending waveforms are possible, thereby minimizing the very aggressive battery charging protocols that exist today in such late systolic absolute refractory period stimulation devices.

Further, the Class DB architectures described herein may be useful for delivery of low and medium voltage therapies for emerging low and medium defibrillation protocols whereby a high voltage shock is only used or delivered after lower voltage therapies have failed to cardiovert or defibrillate. This hybrid amplifier system is capable of delivering near field or far field anti-tachycardia pacing (ATP) to the hot can and may deliver any pinning or synchronized pulses at any rate or frequency of from about 500 ns to about 300 ms to terminate ventricular tachycardia and/or ventricular fibrillation.

The LPF described herein does not use any of the large inductors or capacitors which are always associated with Class D switching PWM power amplifiers. Solid state power semiconductors are employed in concert with software-controlled commands and are delivered to tune the LPFs while the amplifiers are processing the waveforms in real time applications. See FIGS. 5 to 7.

Phase 1 descending BTE waveforms are delivered through a diagonal pair of power transistors, MOSFETs, IGBTs, or any other switching devices through the heart. A Phase 2 waveform is then switched on through the second diagonal transistor pair and delivers the voltage and current through the heart but in a reverse polarity as compared to the Phase 1 waveform. The Phase 2 waveform is also a BTE waveform. Both of the Phase 1 and Phase 2 waveforms are basically a natural capacitive discharge BTE waveform of equation I above. Recent studies have demonstrated that ascending ramp type geometries are not only more effective for defibrillation, but they also significantly reduce damage to the heart muscle. For these reasons, developing miniaturized transvenous ICDs will be much safer and more effective using the new amplifier technologies described herein.

In one aspect of the invention, an apparatus has advanced amplifier classes and LPF technologies for using software generated waveforms that are effective when applying cardiac defibrillation and cardioversion waveforms which significantly reduce damage to the heart muscle.

In another aspect of the invention, an apparatus has Class D and Class B amplifier technologies or architectures to improve ICD, SICD, or similar device efficiency using arbitrary ascending waveforms.

In another aspect of the invention, an apparatus has a new LPF that does not use large power inductors or capacitors for the purpose of attenuating and filtering out the Class D high frequency PWM switching content integrated within the waveform ramp signals.

In another aspect of the invention, an apparatus has Class D amplifier sections for delivering Phase 1 waveform shocks and Class B circuitry for delivering a hard-switched Phase 2 waveform. Phase 2 waveforms may be hard-switched by a circuit external to the amplifier circuit, or the waveforms may be hard-switched using the amplifier software commands.

In another aspect of the invention, a waveform energy control system for controlling software generated waveforms within an implantable cardioverter defibrillator (ICD) comprises differentially driven Class D and Class B amplifier sections, wherein the Class D amplifier section produces Phase 1 ascending waveforms and has a programmable lowpass filter (LPF) and wherein the Class B amplifier section delivers hard-switched Phase 2 waveforms.

In another aspect of the invention, a waveform energy control system for delivering software generated waveforms comprising differentially driven Class D amplifier sections, wherein the Class D amplifier sections produce Phase 1 and Phase 2 ascending waveforms and have a programmable dual plurality LPF.

In another aspect of the invention, in a waveform energy control system, the LPF is designed so that the control system is capable of being used in any power circuit, motor drive, audio power amplifier, or any high power electronics device that requires a high power LPF to filter out any PWM pulses in place of using large inductors and capacitors.

In another aspect of the invention, an implantable device for treating congestive or chronic heart failure in a patient comprises a waveform energy control system for delivering software generated waveforms comprising one or more differentially driven Class D amplifier sections, wherein the Class D amplifier section or sections produce ascending waveforms and have a programmable dual plurality LPF, and wherein intraventicular septum and bundle branches of the patient's heart can be stimulated to increase the ejection fraction of the patient's heart.

In another aspect of the invention, a method comprises using advanced amplifier Classes and LPF technologies in a medical device providing software generated waveforms that are effective when applying cardiac defibrillation and cardioversion waveforms which significantly reduce damage to the heart muscle.

In another aspect of a method of the invention, Class D and Class B amplifier technologies or architectures are combined in a medical device to improve ICD, SICD, AED, or similar device efficiency using arbitrary ascending waveforms.

In another aspect of a method of the invention, a new LPF that does not use large power inductors or capacitors is used in a medical device for the purpose of attenuating the Class D high frequency PWM switching content within the waveform ramp signals.

In another aspect of a method of the invention, one or more Class D amplifier sections are used in a medical device for delivering Phase 1 shocks or waveforms and Class B circuitry is used to deliver hard-switched Phase 2 waveforms.

In another aspect of the invention, a waveform energy control system for treating a cardiac condition in a patient comprises:
 a microcontroller;
 a digital-to-analog converter (DAC);
 an analog to-digital converter (ADC); and
 differentially driven amplifier Class D and Class B circuits each having an input and an output,
wherein the microcontroller is operatively connected to the DAC, the DAC is operatively connected to the input of the differentially driven amplifier circuits, the microcontroller is configured to respond to software commands to generate signals to the DAC, the DAC provides signals to the inputs of the differentially driven amplifier circuits, and the outputs of the differentially driven amplifier circuits delivers constant current, constant voltage, or constant energy ascending arbitrary waveforms, biphasic truncated exponential (BTL) waveforms, or ascending arbitrary waveforms for pacing, near or far field ATP, low-, medium-, or high-voltage therapy, defibrillation, or cardioversion electrical shocks to the patient's heart.

In another aspect of a waveform energy control system of the invention, the cardiac condition treated is ventricular fibrillation (VF) or ventricular tachycardia (VT).

In another aspect of a waveform energy control system of the invention, the waveforms produced are biphasic waveforms comprising a first phase (Phase 1) having a positive voltage potential with respect to a zero voltage crossing point in the form of an ascending ramp, ascending exponential, ascending chopped, ascending stepped, ascending curved, square, rectilinear, BTE, or any combination of geometric-shaped waveforms, followed by a second phase (Phase 2) having a negative voltage potential with respect to a zero voltage crossing point in the form of an ascending ramp, ascending exponential, ascending chopped, ascending stepped, ascending curved, square, rectilinear, BTE, or any combination of geometric-shaped waveforms, to deliver increasing energy with increasing time.

In another aspect of a waveform energy control system of the invention, the Phase 1 and/or Phase 2 defibrillation or cardioversion shock waveforms are produced in response to software commands programmed in the microcontroller.

In another aspect of a waveform energy control system of the invention, shock waveforms are applied internally through a patient's heart and chest and an output waveform is constructed from discrete points in time or equations stored in the microcontroller which at each discrete time point, on the order of microseconds, the microcontroller outputs a new waveform value through the DAC to the amplifiers and at each discrete time point, the current through the patient's heart and chest is converted using an analog-to-digital converter (ADC) wherein a digitized current generated from sense resistors provides electronic feedback to the microcontroller and is sampled at multiple intervals, creating a rolling current average used by the microcontroller and software to calculate power, energy, and voltage in real time for each discrete time point of the output waveform in which the microcontroller then increases or decreases the output waveform to maintain the desired constant current, constant energy, or constant voltage.

In another aspect of a waveform energy control system within an ICD of the invention, the differentially driven amplifier circuits provide arbitrary ascending waveforms, BTE waveforms, or ascending and BTE waveforms with positive voltage and energy Phase 1 time periods from about 1 ms to 300 ms and energy for Phase 2 time periods that can range from about 500 ns to about 10 ms configured as ramp, curved, stepped, BTE, or continuous waveforms using any voltage for Phase 1 and Phase 2 waveforms from about 0 VDC to +/−1500 VDC.

In another aspect of the invention, an implantable cardioverter defibrillator system comprises:
- a subcutaneous case capable of being positioned under a patient's skin in the pectoral area of the patient's upper left chest; and
- a waveform energy control system of the invention located within the subcutaneous case.

In another aspect of the invention, an implantable cardioverter defibrillator system comprises:
- a subcutaneous case capable of being positioned under a patient's skin in the pectoral area of the patient's upper left chest;
- a waveform energy control system of the invention located within the subcutaneous case; and
- a lead wire trans-venously extending from the subcutaneous case and capable of being installed in the patient's right ventricle for pacing, near or far field ATP, low-, medium-, or high-voltage therapy, cardioversion, or defibrillation.

In another aspect of an implantable cardiac defibrillator system of the invention, increasing energy with increasing time is delivered for a positive energy phase of the waveforms and a negative energy phase of the waveforms where only the highest power dissipation portion of a waveform is pulsed or chopped to minimize power dissipation in the output circuits.

In another aspect of an implantable cardiac defibrillator system of the invention, the implantable cardiac defibrillator system is capable of delivering BTE shock waveforms with a tilt angle and waveform pulse width specified via software commands to provide a constant energy, constant voltage, or constant current mode of operation.

In another aspect of an implantable cardiac defibrillator system of the invention, if a shock for defibrillation or cardioversion fails, one or more subsequent shocks or low voltage therapy may be delivered for defibrillation or cardioversion using any arbitrary ascending waveform or BTE waveform saved in the microcontroller memory.

In another aspect of the invention, a subcutaneous implantable cardioverter defibrillator system (SICD) comprises:
- a subcutaneous case capable of being positioned under a patient's skin on the left side of a patient's rib cage;
- a waveform energy control system of the invention located within the subcutaneous case; and
- a lead wire extending from the subcutaneous case and capable of being positioned subcutaneously above or below the patient's sternum for pacing, near or far field ATP, low-, medium-, or high-voltage therapy, cardioversion, or defibrillation.

In another aspect of a subcutaneous implantable cardiac defibrillator system of the invention, the SCID system is controlled via software commands and delivers BTE shock waveforms with a tilt angle and waveform pulse width specified via said software commands to provide a constant current, constant voltage, or constant energy mode of operation.

In another aspect of a subcutaneous implantable cardiac defibrillator system of the invention, if a first shock for defibrillation or cardioversion fails, one or more subsequent shocks or low voltage therapy for defibrillation or cardioversion may be delivered using an arbitrary ascending waveform or BTE waveform saved in the microcontroller memory.

In another aspect of the invention, a method for externally treating a cardiac condition in a patient comprises:
- contacting an area of outer skin of the patient with at least two external multi-electrode patches or paddles that apply current in a rotational manner to pre-stimulate that area;
- in a first step applying a low-voltage electrical current from differentially driven amplifier Class D and Class B circuits having an input and an output beneath the at least two external multi-electrode patches or paddles in a rotational manner to pre-stimulate that area, causing chest muscles beneath the multi-electrode patches or paddles to contract to an absolute refractory period and lowering chest muscles impedance, thereby providing a low impedance chest pathway using less energy compared to standard defibrillation devices; and
- in a second step applying a high voltage arbitrary waveform shock from the multi-electrode patches or paddles through the patient's chest and heart to cause defibrillation and/or cardioversion.

In another aspect of a method of the invention, an amplifier-based external cardioverter defibrillation system is used.

In another aspect of a method of the invention, the cardioversion system uses a two-step electrical stimulation comprising biphasic arbitrary and ascending ramp high-voltage shocks that employ increasing energy with increasing time waveforms which are used to reduce peak voltages, reduce cardioversion and defibrillation energy, capture those patients that don't easily cardiovert or defibrillate, reduce perception of pain and reduce or eliminate burning of skin beneath external electrodes.

In another aspect of a method of the invention, the system uses differentially driven amplifier circuit topologies whereby biphasic arbitrary shock waveforms deliver increasing and or level energy with increasing time as represented by Phase 1 ascending ramp, ascending exponential, ascending chopped, ascending stepped, ascending curved, square, rectilinear or level and or any combination of geometric shaped ascending or level waveforms which are delivered by any selection of three modes of software controlled defibrillation and or cardioversion shock waveforms which are (1) constant current, (2) constant voltage, or (3) constant energy for the purpose of controlling delivered defibrillation and or cardioversion electrical shocks to convert cardiac arrhythmias.

In another aspect of a method of the invention, cardiac arrhythmias are treated.

In another aspect of a method of the invention, qualified medical professionals first apply through mutual electrode delivery patches and use the system's electrical servo amplifier array stimulator to deliver pre-stimulus low voltage pulses to cause skeletal muscle rotation and contraction, comprising the absolute refractory period of muscle contraction and lowering chest impedance.

In another aspect of a method of the invention, in a second step a high voltage Phase 1 time periods of from about 1 ms to 300 ms ascending waveform or any other biphasic arbitrary waveform shock is delivered, whether across the chest or between the front and back of a human chest, for conversion of VT or VF delivering a high-voltage shock ascending or level waveform, which will reduce perceived pain by lowering peak voltages and chest impedance, and also greatly reduce or eliminating the traditional first, second- and sometimes third-degree burns on the patient's skin under external electrodes since arbitrary ramp waveforms and a slower rate of change for the delivered energy are achieved.

In another aspect of a method of the invention, if a first cardioversion or defibrillation shock fails, another shock comprised of different biphasic wave forms may be selected to enhance and capture outlier patients who are difficult to cardiovert or defibrillate thereby increasing the overall rescue rate for patients who require cardioversion and or defibrillation.

In another aspect of a method of the invention, whereby the Phase 2 waveform or shock voltage is "hard-switched" negative with respect to the zero crossing point to any specified negative voltage potential, and preferably, using narrow arbitrary specified Phase 2 waveform pulse widths of between about 1 ms and 10 ms to hyperpolarize the myocardium after the Phase 1 shock has been delivered.

In another aspect of a method of the invention, class A to Z or any other class of amplifier circuit topology is used to process arbitrary waveforms that deliver increasing energy with increasing time for positive Phase 1 waveform time periods of from about 1 ms to 300 ms and negative energy for Phase 2 waveform time periods that can range from about 500 ns to about 10 ms pulsed, chopped, or continuous waveforms using any voltage for Phase 1 and Phase 2 from about 0 V to about +/−2200 VDC.

In another aspect of a method of the invention, a two-step electrical stimulus external pacing delivery system uses ascending or any arbitrary waveforms that are delivered by a servo amplifier array to pace and/or assist in restarting an asystole heart.

In another aspect of the invention, an apparatus for external treatment of a cardiac condition in a patient comprises:
  at least two multi-external electrode patches or paddles for contacting an area of the outer surface of skin of the patient;
  a pre-stimulus servo amplifier array; and
  an external waveform energy software control system which comprises:
    an electronic system containing a microcontroller; and
    external differentially driven Class D and Class B amplifier circuits having an input and an output,
  wherein the microcontroller is operatively connected to the input of the differentially driven amplifier circuits, the microcontroller is configured to respond to software commands to generate signals to the input of the differentially driven amplifier circuits, and the output of the differentially driven amplifier circuits externally delivers constant current, constant energy, or constant voltage ascending arbitrary ramp waveforms, biphasic truncated exponential (BTE) waveforms, or ascending arbitrary and BTE descending waveforms, transcutaneous pacing, low voltage therapies, defibrillation, or cardioversion electrical shocks through the at least two external multi-electrode patches or paddles, through the patient's skin, to the patient's heart, and
    wherein in a first step the pre-stimulus servo amplifier array delivers a low-voltage electrical current beneath the at least two external multi-electrode patches or paddles in a rotational manner to pre-stimulate that area, causing chest muscles beneath the multi-electrode patches or paddles to contract to an absolute refractory period and lowering chest muscle impedance, thereby providing a low impedance chest pathway using less energy compared to standard defibrillation devices, and
    wherein in a second step the differentially driven amplifier circuits deliver a high voltage arbitrary waveform shock from the multi-electrode patches or paddles through the patient's chest and heart to cause defibrillation, cardioversion, or defibrillation and cardioversion.

In another aspect of an apparatus of the invention, the at least two external multi-electrode patches or paddles are capable of delivering transcutaneous external arbitrary pacing pulses and/or low or high voltage therapies through the patient's chest and heart to restart an asystole heart.

In another aspect of a system of the invention, the system uses differentially driven amplifier circuit topologies whereby external biphasic arbitrary shock waveforms deliver increasing and or level energy with increasing time as represented by Phase 1 or Phase 2 ascending ramp, ascending exponential, ascending chopped, ascending stepped, ascending curved, square, rectilinear, BTE, or level and or any combination of geometric shaped ascending or level waveforms which are delivered by any selection of three modes of software controlled defibrillation and/or cardioversion shock waveforms which are (1) constant current, (2) constant energy, or (3) constant voltage for the purpose of controlling delivered defibrillation and/or cardioversion electrical shocks to convert cardiac arrhythmias.

In another aspect of an apparatus of the invention, cardiac arrhythmias are treated.

In another aspect of an apparatus of the invention, the servo amplifier array delivers pre-stimulus low voltage pulses beneath each multi-electrode area to cause skeletal muscle rotation and contraction, comprising the absolute refractory period of muscle contraction and lowering chest muscle impedance.

In another aspect of an apparatus of the invention, the differentially driven amplifier circuits deliver a high voltage ascending arbitrary waveform, BTE, or any other biphasic arbitrary waveform shock, whether across the chest or between the front and back of the chest, for conversion of VT or VF, which reduces perceived pain by lowering peak voltages and chest impedance and also greatly reduces or eliminates burns on the patient's skin under external multi-electrodes.

In another aspect of an apparatus of the invention, if a first cardioversion or defibrillation shock fails, the system software will analyze why the shock failed and cause the apparatus to deliver another external shock comprised of different biphasic waveform geometries to increase capture of outlier patients that are difficult to cardiovert and/or defibrillate, thereby increasing the overall rescue rate.

In another aspect of an apparatus of the invention, the apparatus comprises external differentially driven amplifier circuits to process arbitrary biphasic waveforms that deliver increasing energy with increasing time for positive Phase 1 waveform time periods of from about 1 ms to 300 ms and negative energy for Phase 2 waveform time periods that can range from about 500 ns to about 10 ms pulsed, chopped or continuous waveforms using any voltage for Phase 1 and Phase 2 from about 0 V to about +/−2200 VDC.

In another aspect of an apparatus of the invention, ascending, level, or BTE arbitrary waveforms are delivered by the differentially driven amplifier circuits to pace and/or assist in restarting an asystole heart.

In another aspect of an apparatus of the invention, the external waveform energy control system also comprises a digital-to-analog converter (DAC) and wherein the microcontroller is operatively connected to the DAC, the DAC is operatively connected to the input of the differentially driven amplifier circuits, the microcontroller is configured to respond to software commands to generate signals to the DAC, the DAC provides signals to the input of the differentially driven amplifier circuits, and the output of the differentially driven amplifier circuits delivers constant current, constant voltage, or constant energy employing ascending, level, or BTE-waveform shocks for cardioversion and/or defibrillation, or ascending, level and BTE waveforms for pacing through the patient's heart.

In another aspect of an apparatus of the invention, the waveform energy control system is capable of applying shock waveforms externally through a patient's heart and chest and an output waveform is constructed from discrete points in time or equations stored in the microcontroller which at each discrete time point, on the order of microseconds, the microcontroller outputs a new waveform value through the DAC to the amplifiers and at each discrete time point, the current through the patient's chest and heart is sampled and converted using an analog-to-digital converter (ADC) wherein a digitized current signal is generated from the sense resistors providing electronic feedback to the microcontroller and is sampled at multiple intervals, creating a rolling current average used by the microcontroller and software to calculate power, energy, and voltage in real time for each discrete time point of the output waveform in which the microcontroller then increases or decreases the output waveform amplitude commands to maintain the desired constant current, constant energy, or constant voltage.

In another aspect of an apparatus of the invention, the apparatus is an AED, EMS/EMT, or hospital grade or sports grade cardioverter defibrillator system.

In another aspect of the invention, a system for external treatment of a cardiac condition in a patient comprises:
at least two external multi-electrode patches or paddles for contacting an area of the outer surface of skin of the patient;
a pre-stimulus servo amplifier array;
an external waveform energy software control system which comprises a microcontroller; and
differentially driven amplifier Class D and Class B circuits having an input and an output,
wherein the microcontroller is operatively connected to the input of the differentially driven amplifier circuits, the microcontroller is configured to respond to software commands to generate signals to the input of the differentially driven amplifier circuits and the output of the differentially driven amplifier circuits externally delivers defibrillation or cardioversion electrical shocks through the at least two external multi-electrode patches or paddles, through the patient's skin, to the patient's heart, and
wherein in a first step the pre-stimulus servo amplifier array delivers a low-voltage electrical current beneath the at least two external multi-electrode patches or paddles in a rotational manner to pre-stimulate that area, causing chest muscles beneath the multi-electrode patches or paddles to contract to an absolute refractory period and lowering chest muscle impedance, thereby providing a low impedance chest pathway using less energy compared to standard defibrillation devices, and
wherein in a second step the differentially driven amplifier circuits deliver a high voltage arbitrary waveform shock from the multi-electrode patches or paddles through the patient's chest and heart to cause defibrillation, cardioversion, or defibrillation and cardioversion.

BRIEF DESCRIPTION OF THE DRAWINGS

For a more comprehensive understanding of the invention, reference is made to the following description taken in connection with the accompanying drawings, in which.

DETAILED DESCRIPTION OF THE INVENTION

Unless defined otherwise, all technical and scientific terms used herein have the same meaning as commonly understood to one of ordinary skill in the art to which this invention belongs. Although any methods, devices or materials similar or equivalent to those described herein can be used in the practice or testing of the invention, the preferred methods, devices, and materials are now described.

Figure 1:
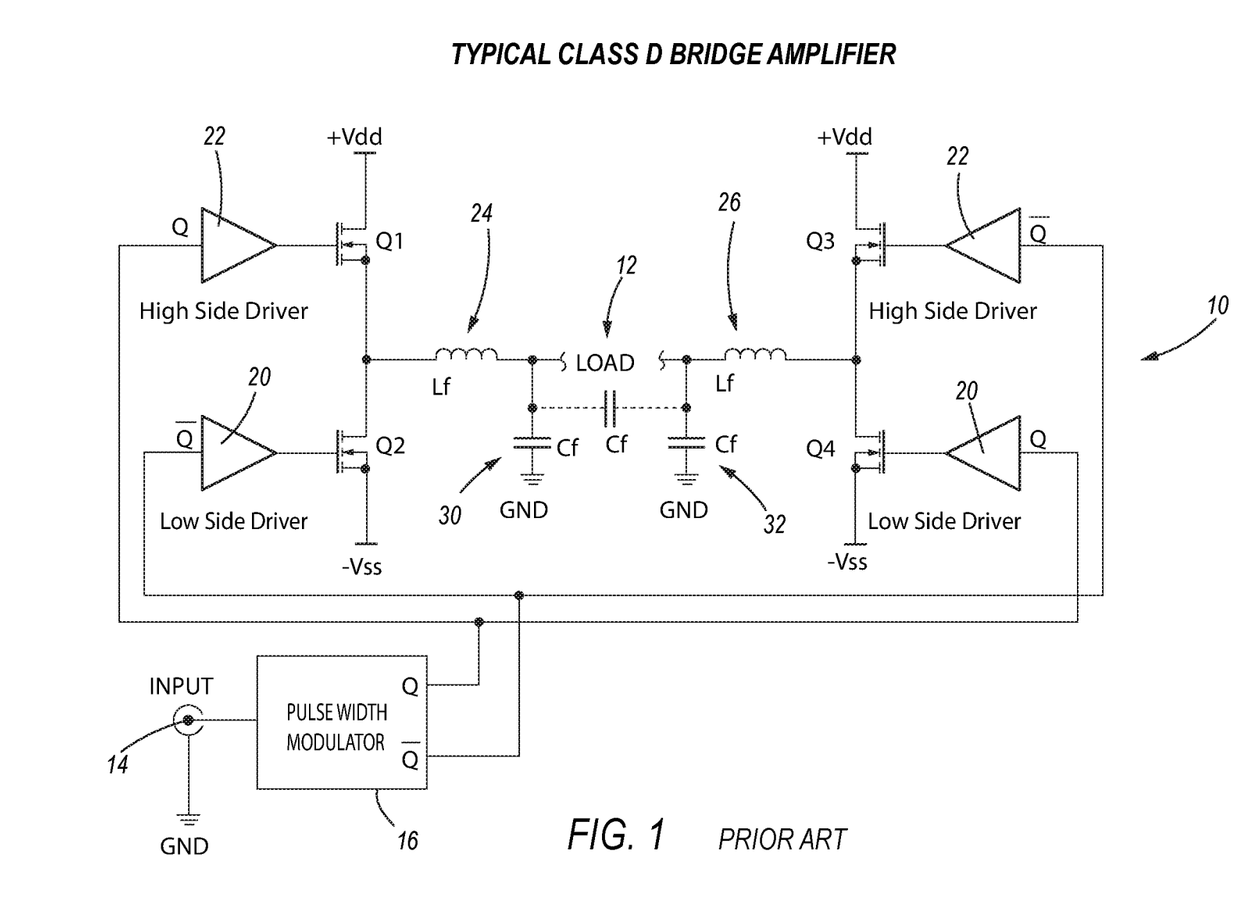
FIG. 1 is a schematic of a typical H-Bridge Class D switching power amplifier. The two large inductors in concert with the two capacitors serve as the LPFs that allow the signal of interest to be delivered into the "load" while attenuating the high frequency PWM switching frequencies to drive the power semiconductors at a very high efficiency.

In FIG. 1, a schematic of a classic H-Bridge Class D amplifier is depicted. The basic operation comprises an H-bridge circuit 10 which differentially drives a low-impedance load 12. A signal from input 14 travels through pulse width modulator 16 to low side drivers 20 and high side drivers 22. The waveform voltage and current in a Class D PWM amplifier has high frequency switching pulses that must be filtered out with an LPF. The LPF comprises high current, high voltage inductors 24, 26 in combination with filter capacitors 30,32. This high frequency filter arrangement allows the signal of interest, in this case an ascending ramp shock waveform, to be delivered to the load 12 with minimal high frequency ripple riding on the fundamental ramp output signal to drive the power semiconductors at a very high efficiency.

Figure 2:
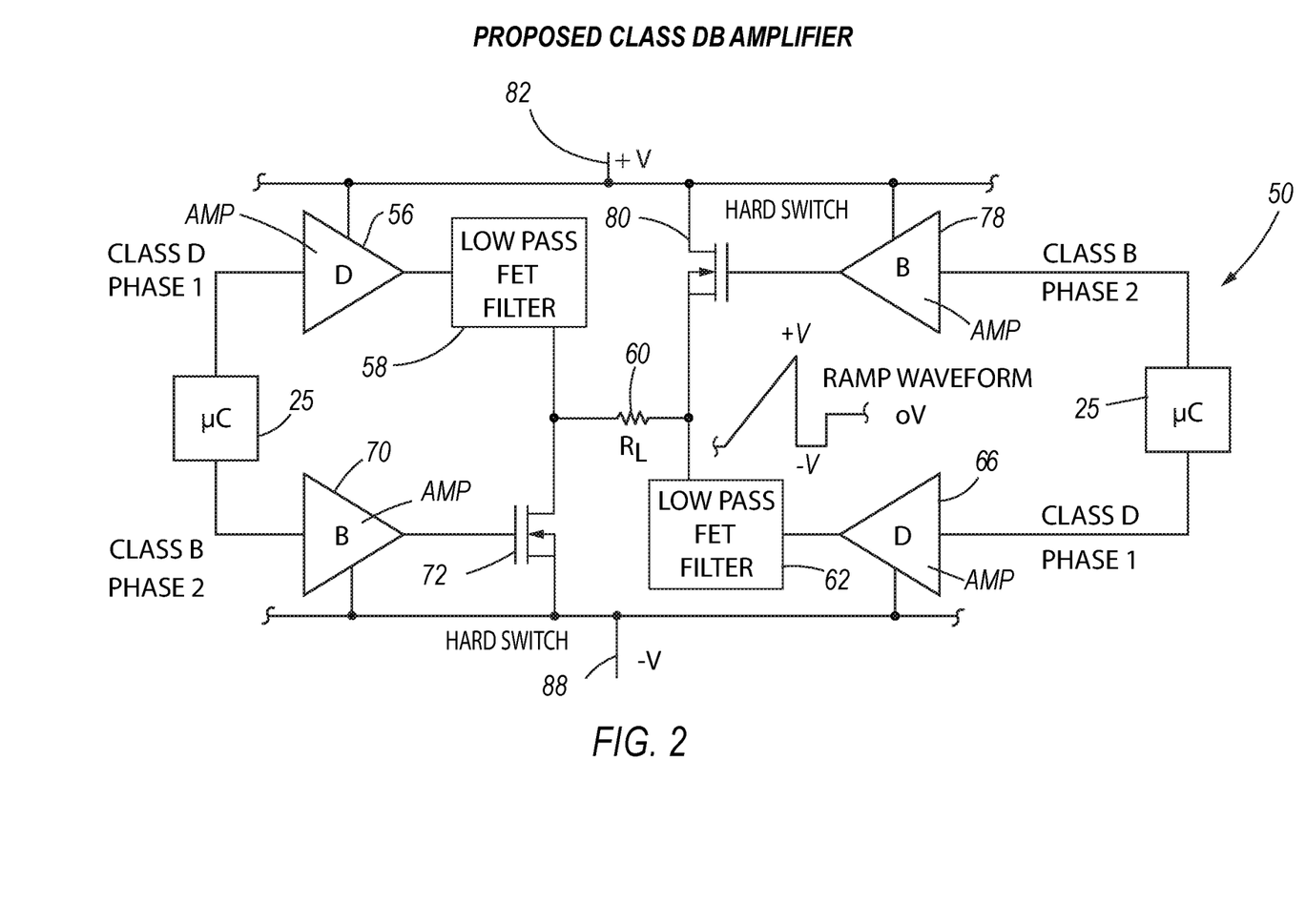
FIG. 2 is a schematic of a new class of hybrid Class DB power amplifier according to the invention whereby Phase 1 and Phase 2 waveforms are delivered into a resistive load.

FIG. 2 is a schematic of a Class DB H-bridge amplifier circuit 50 which uses a power field effect transistor (FET). As shown, a positive phase 1 waveform passing through amplifier 56 is differentially driven through an LPF power FET 58 through the resistive load 60 (which is the heart that will undergo defibrillation). The waveform further travels through a negative LPF 62 and on to a negative amplifier 66. The proposed LPF power FET filters 58,62 replace the large inductors 24,26 as well as the large capacitors 30,32 shown in FIG. 1. Furthermore, a Phase 2 or negative pulse, is delivered through the heart load 60 through Class B amplifiers 70,72 and 78,80 which are driven differentially through the heart load 60. However, these amplifiers are not switched using PWM. Instead, they are hard switched, which will employ a fast slew rate for the negative Phase 2 waveform. At the completion of the Phase 2 waveform, the voltage returns to electrophysiology Zero (EP0), or 0 volts. Amplifier high voltage rails have polarities of plus and minus as depicted 82,88. Class D and B amplifiers are driven differentially by microcontroller 25.

Figure 3:
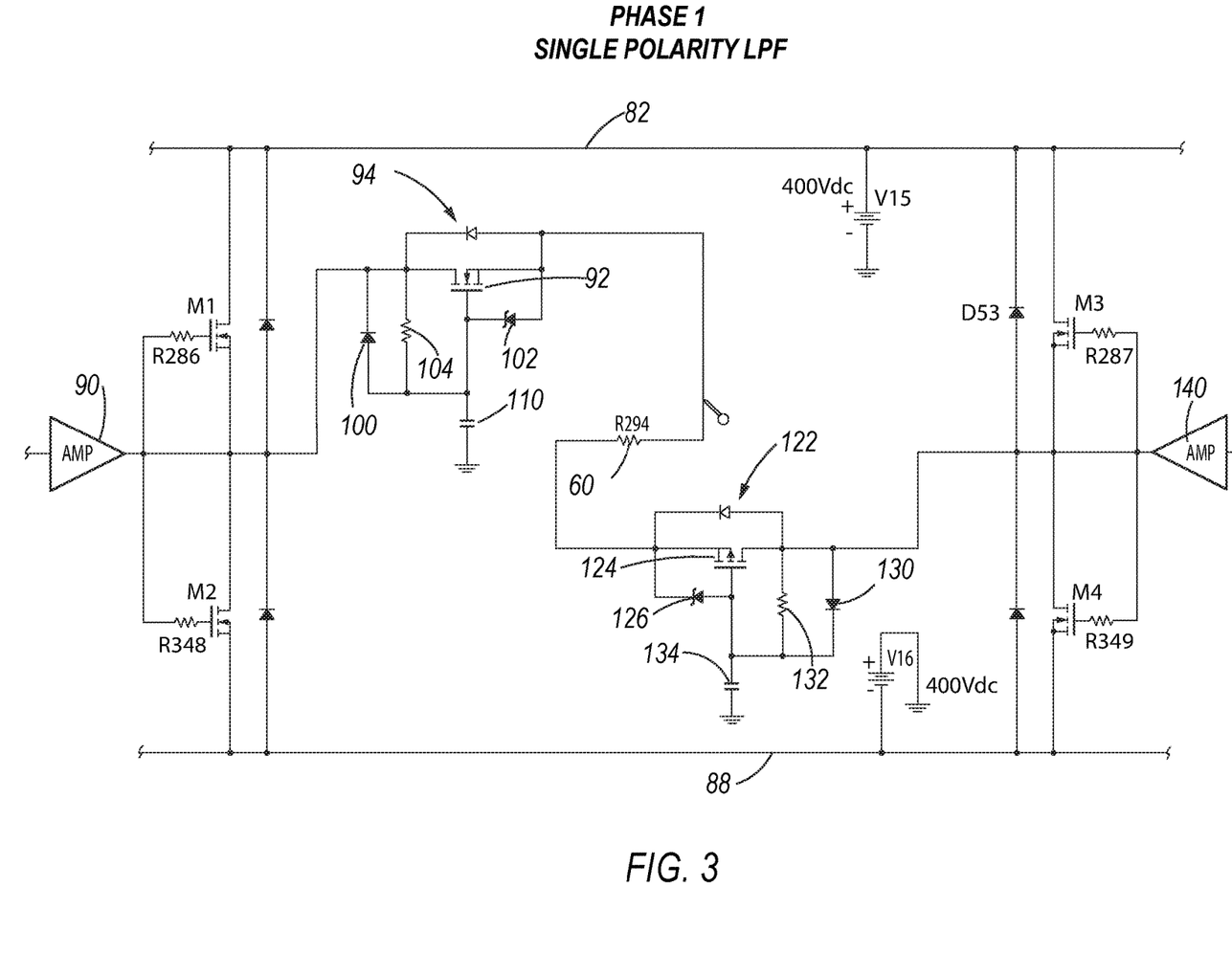
FIG. 3 is a schematic of a new LPF design that employs a solid state high power semiconductor LPF that does not require a large inductor with a magnetic core or large high voltage capacitors. Positive and negative LPFs are employed for the Class D Phase 1 amplifier. A Phase 2 waveform is delivered using the Class B amplifier, which does not require an LPF.

FIG. 3 is a schematic diagram of the circuit of a Phase 1 waveform only LPF. On the left half of the circuit, the output of amplifier 90 drives the LPF, which consists of power FET 92, power diode 94, blocking diode 100, Zener clamp 102, timing resistor 104, and timing capacitor 110. The output of amplifier 90 drives the LPF, which is connected to the heart load 60. On the opposite side of the load 60, the signal is driven through a second LPF for the negative portion of the Phase 1 waveform. This LPF consists of a power diode 122, power FET 124, Zener clamp 126, blocking diode 130, timing resistor 132, and timing capacitor 134. The input to this LPF is driven by amplifier 140.

Figure 4:
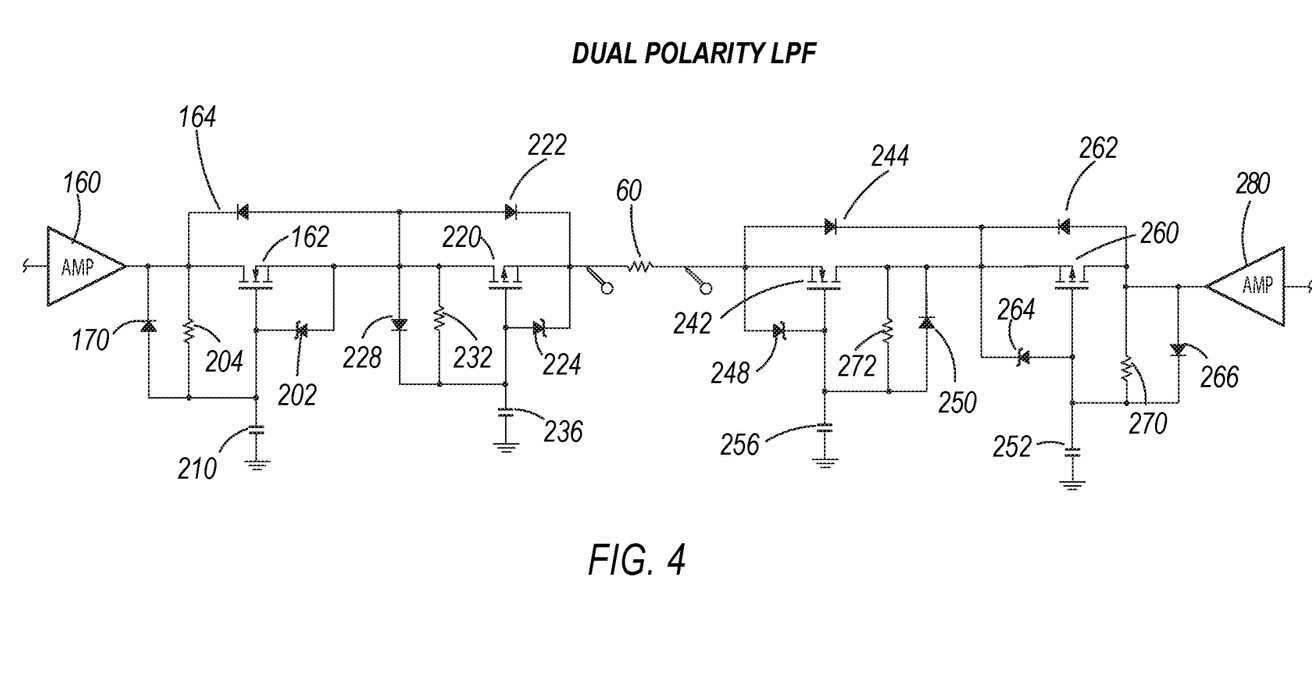
FIG. 4 depicts a dual polarity semiconductor LPF whereby all positive and negative high frequency PWM signals are filtered and attenuated while allowing the waveforms and signals of interest to pass into the load through four Class D amplifiers. The load can be a resistive load, an inductive load, or any appropriate load, including, but not limited to, any power circuit, motor drive, audio power amplifier, or any high power electronics device that requires a high power LPF to filter out any PWM pulses in place of using large inductors and capacitors.

FIG. 4 is a schematic of a dual polarity LPF that may be employed whereby both Phase 1 and Phase 2 waveforms use a Class D PWM circuit topology. Also, both Phase 1 and Phase 2 waveforms have the high frequency PWM switching energy filtered by the new LPF circuits. The output of amplifier 160 drives power FET 162, power diode 164, blocking diode 170, Zener clamp 202, timing resistor 204, and timing capacitor 210. This circuit further connects to the second filter of opposite polarity and drives power FET 220, power diode 222, Zener clamp 224, blocking diode 228, timing resistor 232, and timing capacitor 236. This Phase 1 and Phase 2 biphasic waveform then passes through a heart load 60 for the negative portion of the waveform into power FET 242, power diode 244, Zener clamp 248, blocking diode 250, timing resistor 272, and timing capacitor 256. The output of this filter section drives the opposite polarity filter through power FET 260, power diode 262, Zener clamp 264, blocking diode 266, timing resistor 270, and timing capacitor 252, returning through Class D amplifier 280. This filter arrangement provides a complete replacement for the two large inductors and two large capacitors 24,26,30,40 for a full Class D amplifier configuration.

Figure 5:
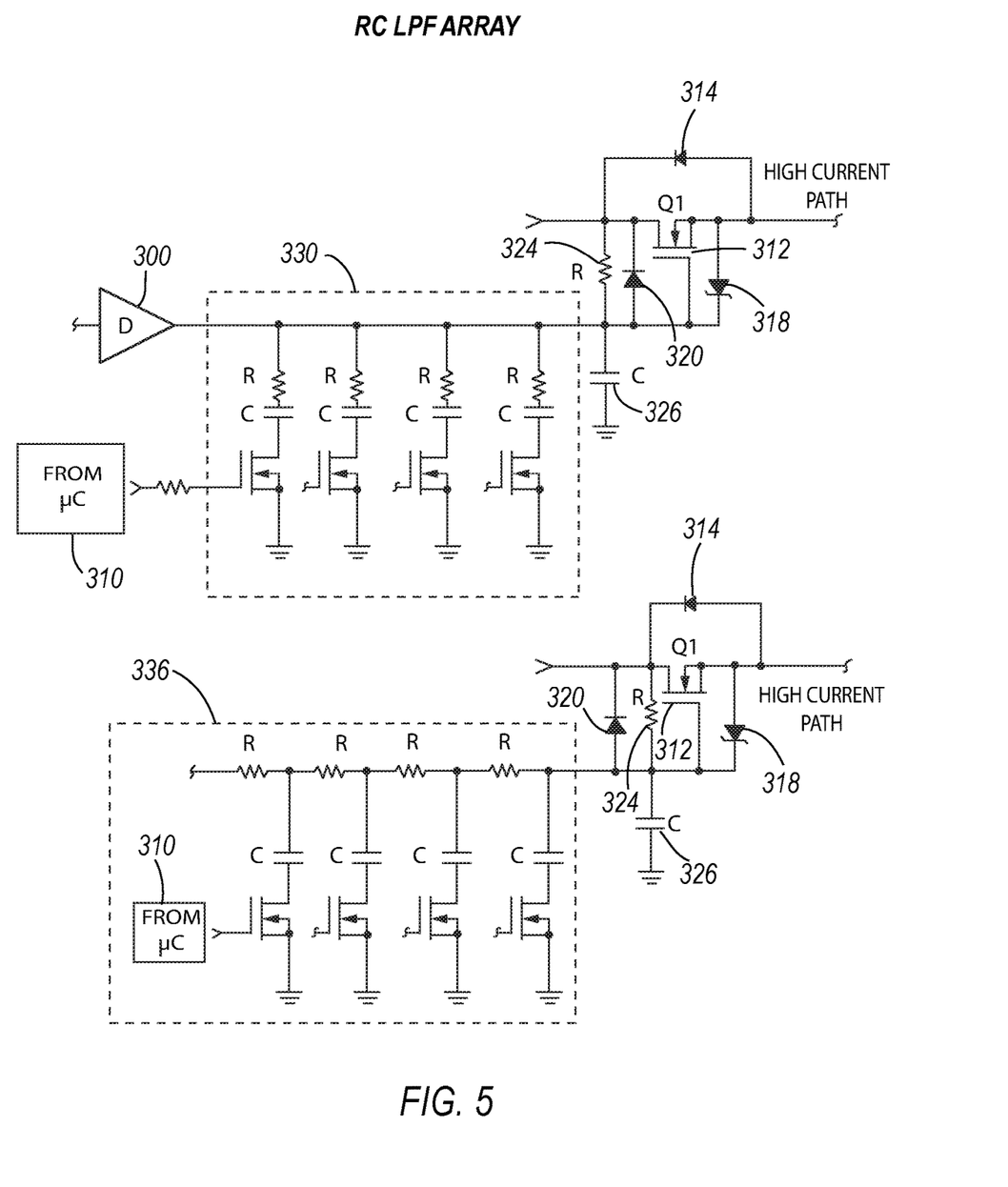
FIG. 5 shows different LPF array tunable circuits whereby a microcontroller manages several resistor/capacitor (RC) low current, LPFs in real time based upon the changing chest and heart impedance to optimize and miniaturize the new LPF that replaces the old style inductor, capacitor LPF. The purpose of a real time tunable filter is to minimize ripple filter from the waveform or signals of interest and to employ smaller LPF components that facilitate miniaturization.

FIG. 5 represents a schematic of a microcontroller digital resistor capacitor (RC) LPF array 330 which provides very specific high frequency filtering while simultaneously tracking the heart and chest impedance from the beginning of an ascending ramp waveform shock to the peak voltage of an ascending ramp shock. This filter array will change its characteristics dynamically and progressively throughout the waveform delivery. The signal coming from the output of amplifier 300 will be driven into an RC LPF array 330 which consists of two or more combinations of R, C, and FET switches as commanded from microcontroller 310. The microcontroller 310 will sample and track the chest and heart impendence and make adjustments to the dynamic LPF array in conjunction with the appropriate power FET 312, power diode 314, Zener clamp 318, blocking diode 320, timing resistor 324, and timing capacitor 326. This RC LPF array 330 circuitry is repeated for single or dual polarity LPFs for one or both amplifiers within the system. In another embodiment of an RC LPF array 336, a different configuration of the RC connectivity is used which will be commanded from a microcontroller 310 and will still be driven in conjunction with the appropriate power FET 312, power diode 314, Zener clamp 318, blocking diode 320, timing resistor 324, and timing capacitor 326.

Figure 6:
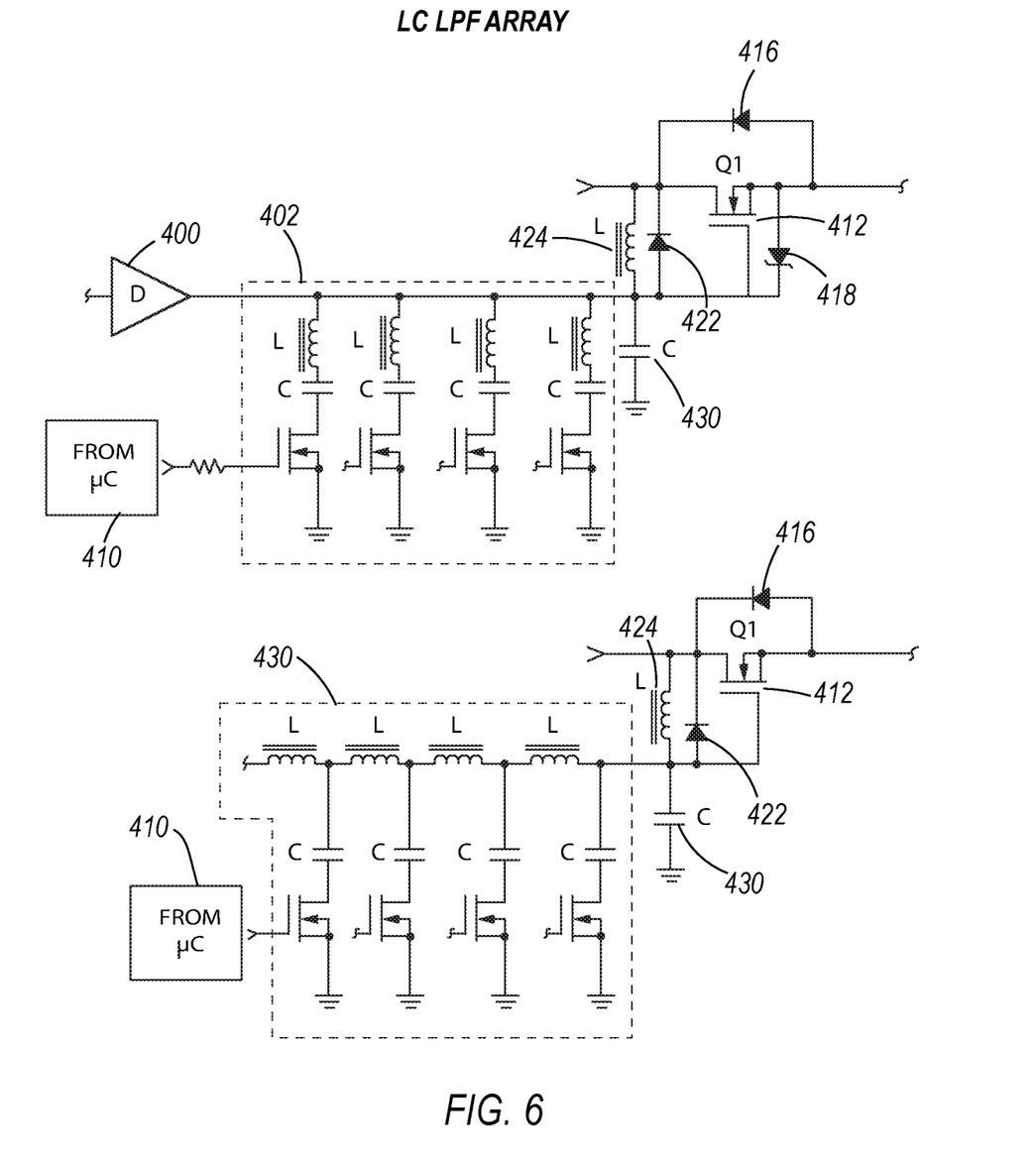
FIG. 6 depicts different LPF array tunable circuits whereby a microcontroller manages several inductor/capacitor (LC) low current, LPFs in real time based upon the changing chest and heart impedance to optimize and miniaturize the LPF that replaces the old style inductor, capacitor LPF. The purpose of a real time tunable filter is to minimize ripple filter from the waveform or signals of interest and to employ smaller LPF components that facilitate miniaturization while simultaneously tracking and adjusting for the changing chest and heart impedance.

FIG. 6 represents a schematic of a microcontroller digital inductor capacitor (LC) LPF which provides very specific high frequency filtering while simultaneously tracking the heart and chest impedance from the beginning of an ascending ramp waveform shock to the peak voltage of an ascending ramp shock. This filter will change its characteristics dynamically and progressively throughout the waveform delivery. The signal coming from the output of amplifier 400 will be driven into an LC LPF array 402 which consists of two or more combinations of L, C, and FET switches as commanded from microcontroller 410. The microcontroller 410 will sample and track the chest and heart impendence and make adjustments to the dynamic LC LPF array in conjunction with the appropriate power FET 412, power diode 416, Zener clamp 418, blocking diode 422, timing inductor 424, and timing capacitor 430. This LC LPF array 402 circuitry is repeated for single or dual polarity LC LPFs for one or both amplifiers within the system. In another embodiment of an LC LPF array 430, a different configuration of the LC connectivity is used which will be commanded from the microcontroller 410 and will still be driven in conjunction with the appropriate power FET 412, power diode 4160, Zener clamp 418, blocking diode 422, timing inductor 424, and timing capacitor 430.

Figure 7:
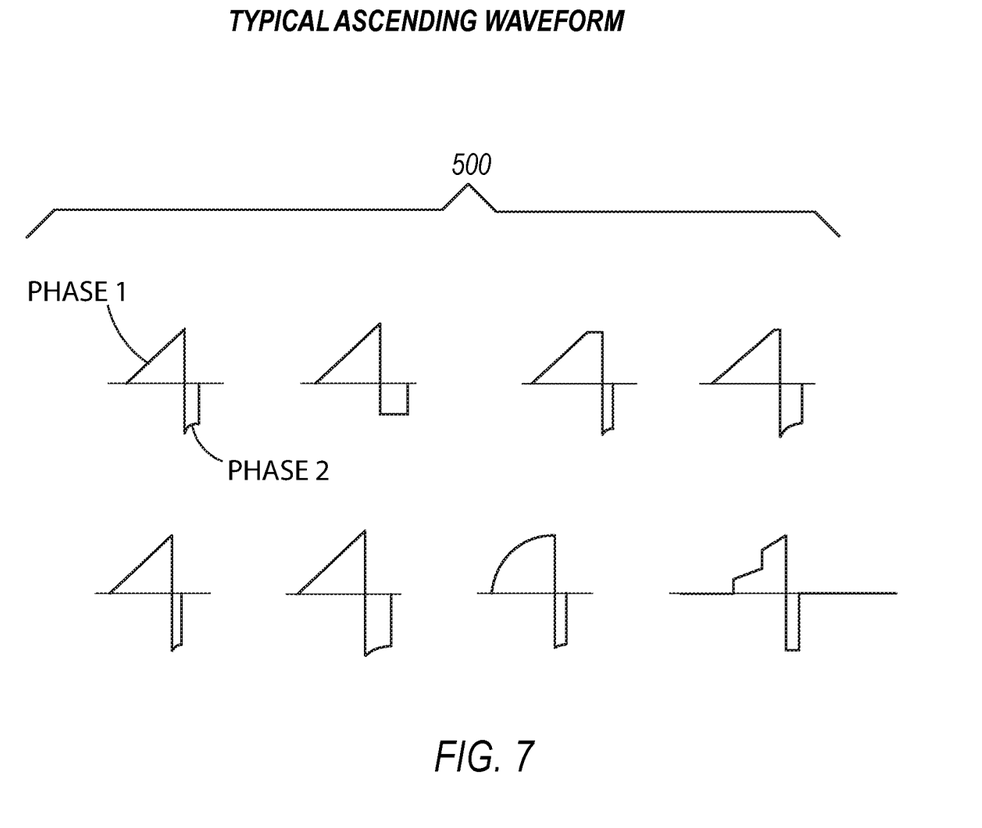
FIG. 7 represents typical examples of ascending waveforms that have been used in animal studies to deliver increasing energy with increasing time as compared to the standard BTE waveforms that can only deliver decreasing energy with increasing time.

FIG. 7 depicts a few possible Phase 1 and Phase 2 ascending ramp waveforms 500.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

We claim:

1. A waveform energy control system for delivering software generated waveforms within a subcutaneously implantable cardioverter defibrillator comprising differentially driven Class D and Class B amplifier sections, wherein the Class D amplifier section produces Phase 1 ascending waveforms and has a programmable impedance tracking lowpass filter (LPF) and wherein the Class B amplifier section delivers fast slew rate, hard-switched Phase 2 waveforms.

2. The control system of claim 1 wherein the Class D amplifier section does not use large power inductors or large capacitors to filter and attenuate high frequency pulse width modulation (PWM) switching content of the Class D amplifier section wherein the Phase 1 ascending ramp waveform signals are produced.

3. The control system of claim 1, wherein the control system is configured to generate ascending waveforms which significantly reduce damage to a patient's heart muscle when cardiac defibrillation or cardioversion electrical shocks are applied.

4. A controller for a cardiac device to treat a cardiac condition in a patient, which comprises:
a microcontroller;
a digital-to-analog converter (DAC);
an analog to digital converter (ADC); and
a waveform energy control system comprising differentially driven Class D and Class B amplifier sections, wherein the Class D amplifier section produces Phase 1 ascending waveforms and has a programmable impedance tracking lowpass filter (LPF) and wherein the Class B amplifier section delivers fast slew rate, hard-switched Phase 2 waveforms,
wherein each of the Class D and Class B amplifier sections has an input and an output,
wherein the microcontroller is operatively connected to the DAC, the DAC is operatively connected to each of the inputs of the Class D and Class B amplifier sections, the microcontroller is configured to respond to software commands to generate signals to the DAC, the DAC provides signals to the inputs of the Class D and Class B amplifier sections, and the outputs of the Class D and Class B amplifier sections deliver constant current, constant voltage, or constant energy ascending arbitrary waveforms or biphasic truncated exponential (BTE) waveforms for pacing, anti-tachycardia pacing (ATP), low-, medium-, or high-voltage therapy, cardioversion or defibrillation electrical shocks to the patient's heart or for providing a late systolic electrical impulse to stimulate the intraventricular septum and bundle branches of the patient's heart to increase the heart's ejection fraction.

5. The controller of claim 4, wherein the Phase 1 waveforms have time periods of from about 1 ms to 300 ms and the Phase 2 waveforms have time periods of from about 500 ns to about 10 ms, configured as ramp, curved, stepped, or BTE waveforms using any voltage of from about 0 VDC to +/−1500 VDC for Phase 1 and Phase 2.

6. The controller of claim 4, wherein the patient receives pacing therapy, near or far field ATP, low-, medium-, or high-voltage therapy, or cardioversion or defibrillation electrical shocks to the patient's heart.

7. The controller of claim 4, wherein the cardiac condition treated is ventricular fibrillation (VF) or ventricular tachycardia (VT).

8. The controller of claim 4, wherein the waveforms produced are biphasic waveforms comprising a first phase (Phase 1) having a positive voltage potential with respect to a zero voltage crossing point in the form of an ascending ramp, ascending exponential, ascending chopped, ascending stepped, ascending curved, square, rectilinear, BTE, or any combination of geometric-shaped waveforms, followed by a second phase (Phase 2) having a negative voltage potential with respect to a zero voltage crossing point in the form of an ascending ramp, ascending exponential, ascending chopped, ascending stepped, ascending curved, square, rectilinear, BTE, or any combination of geometric-shaped waveforms, to deliver increasing energy with increasing time.

9. The controller of claim 8, wherein the Phase 1 or Phase 2 defibrillation or cardioversion shock waveforms are produced in response to software commands programmed in the microcontroller.

10. The controller of claim 4, wherein shock waveforms are applied internally through a patient's heart and chest and an output waveform is constructed from discrete points in time or equations stored in the microcontroller which at each discrete time point, on the order of microseconds, the microcontroller outputs a new waveform value through the DAC to the amplifiers and at each discrete time point, the current through the patient's heart and chest is converted using an analog-to-digital converter (ADC) wherein a digitized current generated from sense resistors provides electronic feedback to the microcontroller and is sampled at multiple intervals, creating a rolling current average used by the microcontroller and software to calculate power, energy, and voltage in real time for each discrete time point of the output waveform in which the microcontroller then increases or decreases the output waveform to maintain the desired constant current, constant energy, or constant voltage.

11. An implantable cardioverter defibrillator device (ICD), which comprises:
a subcutaneous case capable of being positioned under a patient's skin in the pectoral area of the patient's upper left chest;
a controller of claim 5 located within the subcutaneous case; and
a lead wire trans-venously extending from the subcutaneous case and capable of being installed in the patient's right ventricle for pacing, near or far field ATP, low-, medium-, or high-voltage therapy, cardioversion or defibrillation electrical shocks to the patient's heart or for providing a late systolic electrical impulse to stimulate the intraventricular septum and bundle branches of the patient's heart to increase the heart's ejection fraction.

12. The implantable cardioverter defibrillator device of claim 11 which is capable of delivering BTE shock waveforms with a tilt angle and waveform pulse width specified via software commands to provide a constant energy, constant voltage, or constant current mode of operation.

13. The implantable cardioverter defibrillator device of claim 11, wherein, if a shock for defibrillation or cardioversion fails, one or more subsequent voltage pulses, shocks or low-, medium-, or high-voltage therapy may be delivered for defibrillation or cardioversion using any arbitrary ascending waveform or BTE waveform saved in a microcontroller memory.

14. A subcutaneous implantable cardioverter defibrillator device (SICD), which comprises:
a subcutaneous case capable of being positioned under a patient's skin on the left side of a patient's rib cage;

a controller of claim 4 located within the subcutaneous case; and a lead wire extending from the subcutaneous case and capable of being positioned subcutaneously above or below the patient's sternum for pacing, far field ATP, low-, medium-, or high-voltage therapy, cardioversion or defibrillation electrical shocks to a patient's heart or for providing a late systolic electrical impulse to stimulate the intraventricular septum and bundle branches of the patient's heart to increase the heart's ejection fraction.

15. The subcutaneous implantable cardioverter defibrillator device of claim 14, wherein, if a first shock for defibrillation or cardioversion fails, one or more subsequent shocks or low-, medium-, or high-voltage therapy for defibrillation or cardioversion may be delivered using an arbitrary ascending waveform or BTE waveform saved in a microcontroller memory.

* * * * *